United States Patent
Lappe

[11] Patent Number: 5,916,815
[45] Date of Patent: Jun. 29, 1999

[54] ASSAYING SYSTEM FOR ILLICIT SUBSTANCES USING INTENTIONAL FALSE POSITIVES TO INITIALLY PRESERVE ANONYMITY

[75] Inventor: Murray Lappe, Beverly Hills, Calif.

[73] Assignee: National Medical Review Office Inc., Los Angeles, Calif.

[21] Appl. No.: 08/801,041

[22] Filed: Feb. 14, 1997

[51] Int. Cl.⁶ .................. G01N 33/00; G01N 21/77; G01N 21/00; G01N 15/06
[52] U.S. Cl. .................. 436/92; 436/96; 436/98; 436/111; 436/169; 422/56; 422/58; 422/68.1
[58] Field of Search .............. 422/56, 58, 68.1; 436/92, 96, 98, 111, 169, 901

[56] References Cited

U.S. PATENT DOCUMENTS

| | | | |
|---|---|---|---|
| 3,832,134 | 8/1974 | Sohn | 23/230 |
| 4,844,866 | 7/1989 | Wallace et al. | 422/56 |
| 4,873,193 | 10/1989 | Jensen et al. | 436/176 |
| 4,992,296 | 2/1991 | Gibson | 427/2 |
| 5,009,235 | 4/1991 | Messenheimer | 128/760 |
| 5,039,616 | 8/1991 | Copelan | 436/56 |
| 5,133,935 | 7/1992 | Copelan | 422/61 |
| 5,200,321 | 4/1993 | Kidwell | 435/7.9 |
| 5,356,782 | 10/1994 | Moorman et al. | 435/7.9 |
| 5,464,775 | 11/1995 | Smith | 436/63 |
| 5,516,638 | 5/1996 | Urnovitz et al. | 435/7.32 |
| 5,541,059 | 7/1996 | Chu | 435/5 |

OTHER PUBLICATIONS

Swotinsky et al., J. Occup. Med. 32(10), 1003–1008 (1990) (abstract only).
Osterloh et al., J. Psyco. Drugs 22(4), 407–417 (1990) (abstract only).

*Primary Examiner*—Kenneth R. Horlick
*Attorney, Agent, or Firm*—Goldstein & Canino

[57] ABSTRACT

An assaying system for determining the presence of particular illicit substances in human physiological fluid, consisting of a collection cup, a collection cup lid, and a test card with assaying means, quality control means and adulteration detection means which is secured to the collection cup lid. The assaying means contemplate the addition of control positives such that a pre-determined number of assaying systems would be configured so that a false positive indication would be given by the assaying means in addition to any true positive results which may be present. Accordingly, it would initially be impossible to distinguish true test-positives from control positives, and thus the anonymity of a true test-positive donor individual would be protected. All donor individuals testing negative would be immediately discernible.

9 Claims, 3 Drawing Sheets

ASSAYING SYSTEM FOR ILLICIT SUBSTANCES USING INTENTIONAL FALSE POSITIVES TO INITIALLY PRESERVE ANONYMITY

BACKGROUND OF THE INVENTION

The invention relates to an assaying system. More particularly, the invention relates to an assaying device and container for analyzing a specimen of body fluid to detect the absence of particular substances therein, said assaying device employing a positive control, a negative control, and adulteration test. More specifically, the invention relates to an assaying system employing a test card having assaying means such as chromatograph strips located thereupon, the assaying means having a built-in positive control. Furthermore, adulteration means are also employed by the assaying device to ensure the integrity of the specimen of body fluid collected in the container.

The increase in drug use over the past several decades has created a sharp need for more effective, expeditious methods of analyzing whether a particular individual is a user of certain illegal substances. Both private industry employers as well as governmental employers often need to determine whether an individual has drug residue present in his or her biological system, and hence determine whether such an individual is a drug user or drug abuser and thus an undesirable employee.

Typically, the status of an individual as a drug user or abuser is determined by analysis of the individual's physiological fluids, namely urine. A specimen of urine is collected, and an initial screening test is first performed, usually at a centralized laboratory. If specimen samples screen positive at the central laboratory, then a more sensitive and controlled confirmation analysis must be performed and reviewed by a certified "medical review office" where licensed physicians must confirm the positive results detected by the central laboratory.

In addition to being an extremely costly process, the above mentioned procedure also involves great time delays to employers desirous of obtaining new qualified employees. Upon collection of the urine sample, the employer must wait to receive test results from the central laboratory before hiring any potential employees. Furthermore, the massive amount of handling and transfer of the sample of urine from the initial collection site to the central laboratory and then possibly to a medical review office increases the possibility of contamination and mis-identification of the specimen, and raises various chain of custody problems.

To combat the above mentioned timeliness problem which faces many employers in awaiting results from the central laboratory, various "on-site" or "hand-held" assaying devices have been developed. A major problem inherent in these "on-site" testing devices is that the privacy concerns of the potential employee being tested are not adequately addressed. Since all of the on-site testing devices available heretofore attempt merely to identify drugs present (i.e. simply to indicate which specimens do indeed possess the prohibited substance/drug), the anonymity of a presumptive positive donor is impossible to conceal. Since the definitive positive test results must be determined by a certified laboratory, all "on-site" information utilizing current devices would carry a certain amount of stigma associated with a positive test. The positive donor's status can also be inferred by others due to the fact that his or her employment application is immediately handled differently than those donors who do not test "positively". Due to such lack of anonymity, many employers (governmental in particular) will not employ such an assaying system as it does not comply with federally mandated regulations regarding privacy and civil liberties during drug-employment testing. A more anonymous, reliable and expeditious assaying system is needed, wherein negative results can be obtained quickly without compromising the privacy concerns of the tested individual.

Assaying systems, such as the types discussed above, often tend to lack proper collection and storage means. Commonly, a specimen of physiological fluid such as urine is gathered and stored in one type of collection unit, and then the assaying means are either introduced into the collection unit, or a small volume of the urine specimen is removed from the collection unit and placed upon the assaying device. The various transfers of fluid samples pose a great threat of contamination of the sample, as well as mis-identification. A system which allows collection and assaying of a specimen within one unit would lessen these risks.

Many assaying systems available on the market attempt to ensure the quality and reliability of each individual test by employing a "negative control" to inform the user that the reagents or antibodies used as the assaying means are functioning properly. A signal from the negative control informs the user/administrator of the test that the assaying means have not been compromised. Failure to receive an indication from the negative control can indicate that the integrity of the test has been impinged due to improper storage or handling, and that the assaying unit should be discarded. While this negative control does allow for quality control of the integrity of the diagnostic assay means, it in no way provides any quality control assurances regarding the integrity of the specimen collected. Due to civil liberty concerns, specimen donors are usually permitted a great amount of privacy when providing the specimen. The potential for tampering with the specimen is great, and is in no way addressed by the negative control assurances which deal only with the integrity of the assay means itself. An assaying system possessing some sort of adulteration detecting means is needed in the art to ensure the integrity of the specimen being analyzed.

Assaying systems available on the market attempt to identify the presence of illicit drugs by labeling each assay and making no provisions for the inherent unreliability due to cross reactivity of on site devices. A device which incorporates no assay labels as well as a 5% to 10% positive control would ensure that 90% of the tested population could be immediately available for "hire" or "return to work", while 10% of those tested would require additional central laboratory testing. By including a 5% to 10% positive control, no on-site employer could determine from the results of the on-site test whether the donor was truly positive or simply utilized a control positive collection device.

Accordingly, various types of assaying systems are found in the art, each one lacking one or more much needed traits. For instance, U.S. Pat. No. 4,992,296 to Gibson and 5,356,782 to Moorman et al. are typical references found in the art. While these units may be suitable for the particular purpose employed, or for general use, they would not be as suitable for the purposes of the present invention as disclosed hereafter.

SUMMARY OF THE INVENTION

It is an object of the invention to produce an assaying system for analyzing a specimen of body fluid to detect the absence of particular substances therein.

It is another object of the invention to provide an assaying system which provides more anonymous, reliable and expeditious results than those assaying systems presently found in the art, wherein said results can be obtained quickly without compromising the privacy concerns of the tested donor individual.

It is a further object of the invention to provide an on-site, portable assaying system which allows the results of said assay to be determined and utilized immediately by an employer, without jeopardizing the privacy rights of the individual being tested.

It is a still further object of the invention to provide an assaying system which allows collection and assaying of a specimen within one unit so that the amount of handling of said specimen is lessened, and with it the risk of contamination or mis-identification is also decreased.

It is yet another object of the invention to provide an assaying system which possesses means capable of detecting adulteration of the specimen.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
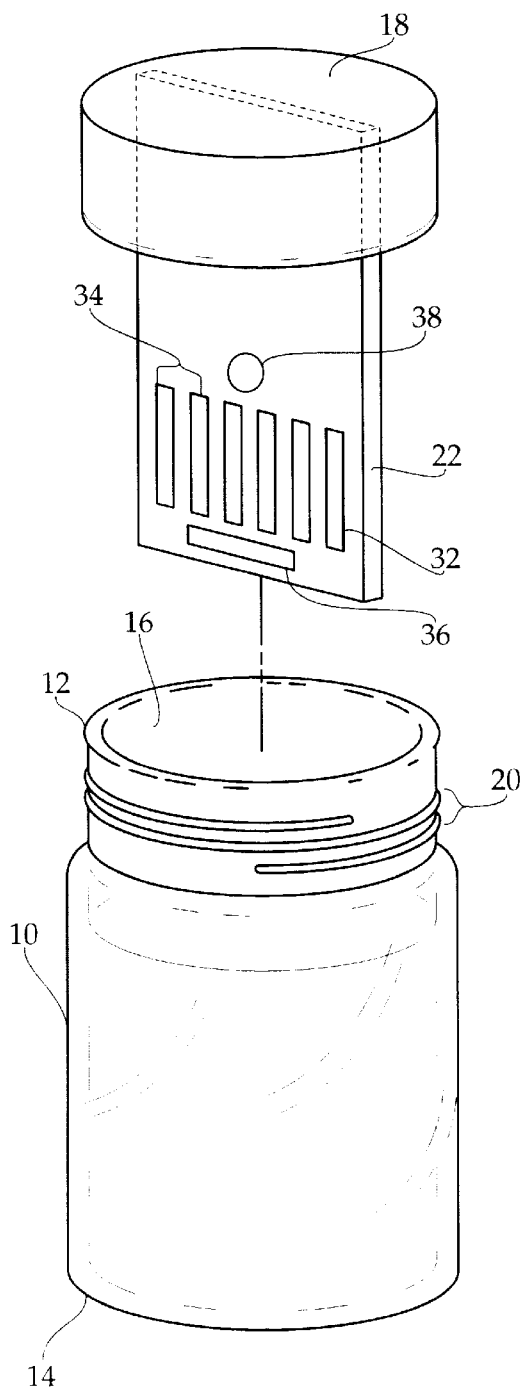
FIG. 1 is a diagrammatic perspective view of a collection cup and collection cup lid with a test card attached perpendicular thereto.

FIG. 1 illustrates a first embodiment of an assaying system. Shown is a collection cup 10, having an upper end 12, a lower end 14, and an opening 16 located at the upper end 12. The collection cup 10 may be formed or molded from any suitable material such as plastic or glass. A collection cup lid 18 is also shown, said collection cup lid 18 substantially similar in size to the diameter of the collection cup 10. Screw threads 20 are formed into the collection cup 10 proximate the opening 16 at the upper end 12, for accepting the collection cup lid 18. The collection cup lid 18, when screwed onto said screw threads 20, provides a means for sealing the opening 16.

Figure 2:
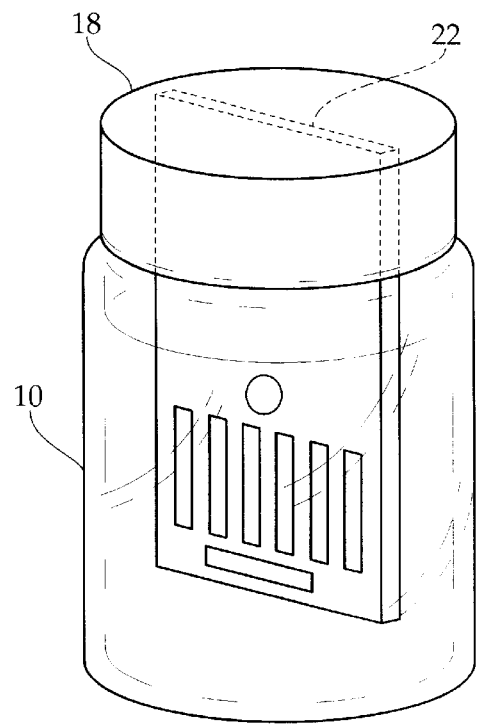
FIG. 2 is a diagrammatic perspective view of the collection cup and collection cup lid in an assembled state.
Figure 3A:
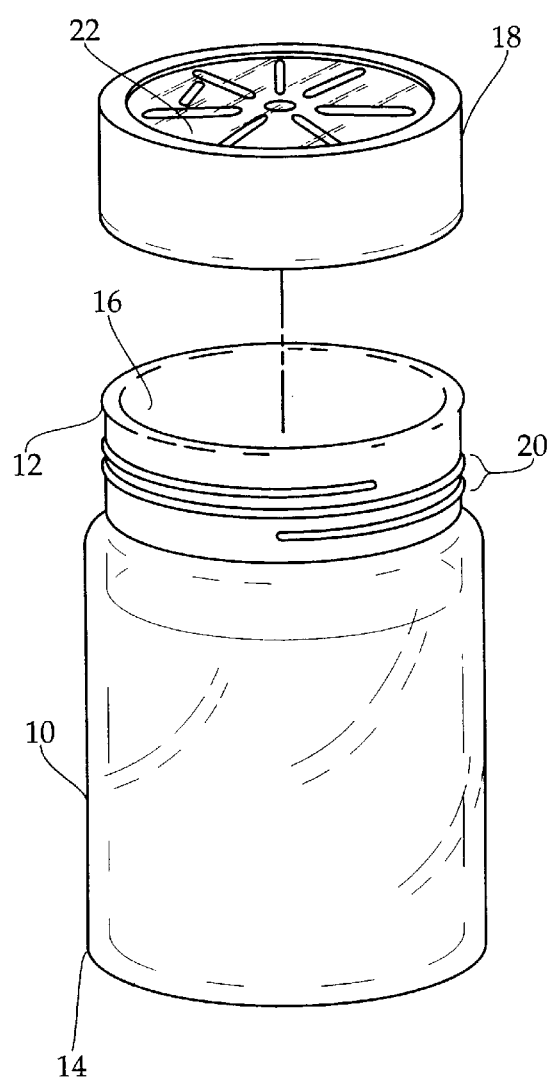
FIG. 3A is a diagrammatic perspective view of a second embodiment of the collection cup and collection cup lid, wherein the test card is circular in shape and secured within a transparent cavity of the collection cup lid.
Figure 3B:
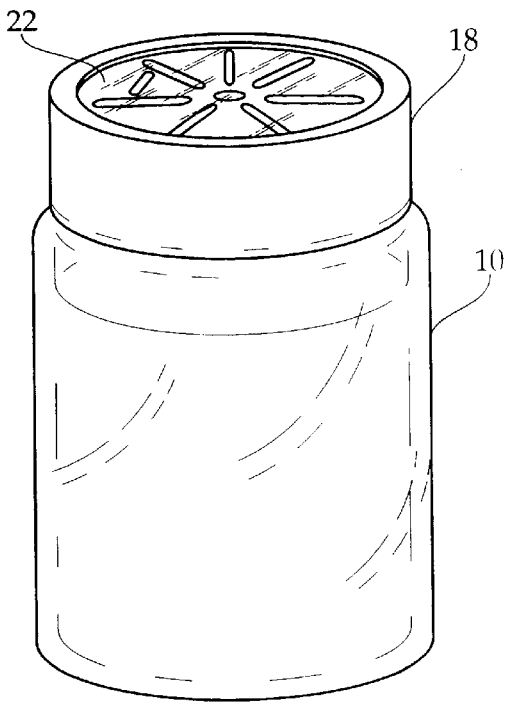
FIG. 3B is a diagrammatic perspective view of the embodiment depicted in FIG. 3A, shown in an assembled state.

Also shown in FIG. 1 is a test card 22, affixed perpendicular to the collection cup lid 18 and extending downward, so that when the collection cup lid 18 is screwed onto the screw threads 20 of the collection cup 10, the test card 22 extends through the opening 16 located thereat and is enveloped within the collection cup 10, as seen fully in FIG. 2.

To employ this first embodiment of the assaying system, a volume of physiological fluid such as urine is collected from a donor individual and deposited in the collection cup 10. The collection cup lid 18 is then secured to the collection cup 10, such that the test card 22 is partially or wholly immersed in said urine. The assembled collection cup 10 and collection cup lid 18 is then inverted several times and shaken to assure that the volume of urine or other physiological fluid sufficiently contacts all areas of the test card 22. The volume of urine or similar fluid is then analyzed by the test card 22 and visual analysis results are provided thereon, immediately visible through the collection cup 10.

Figure 4:
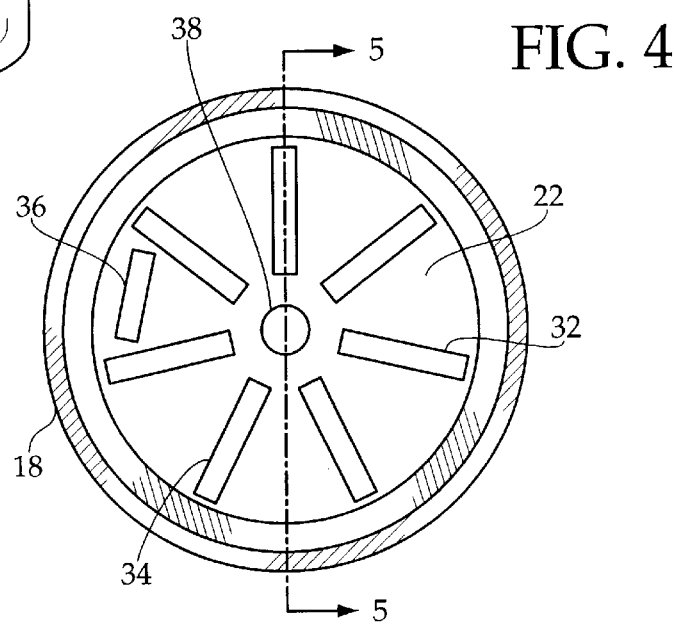
FIG. 4 is a plan view of the collection cup lid of FIG. 3A, depicting the test card, circular in shape, contained and visible therein.
Figure 5:
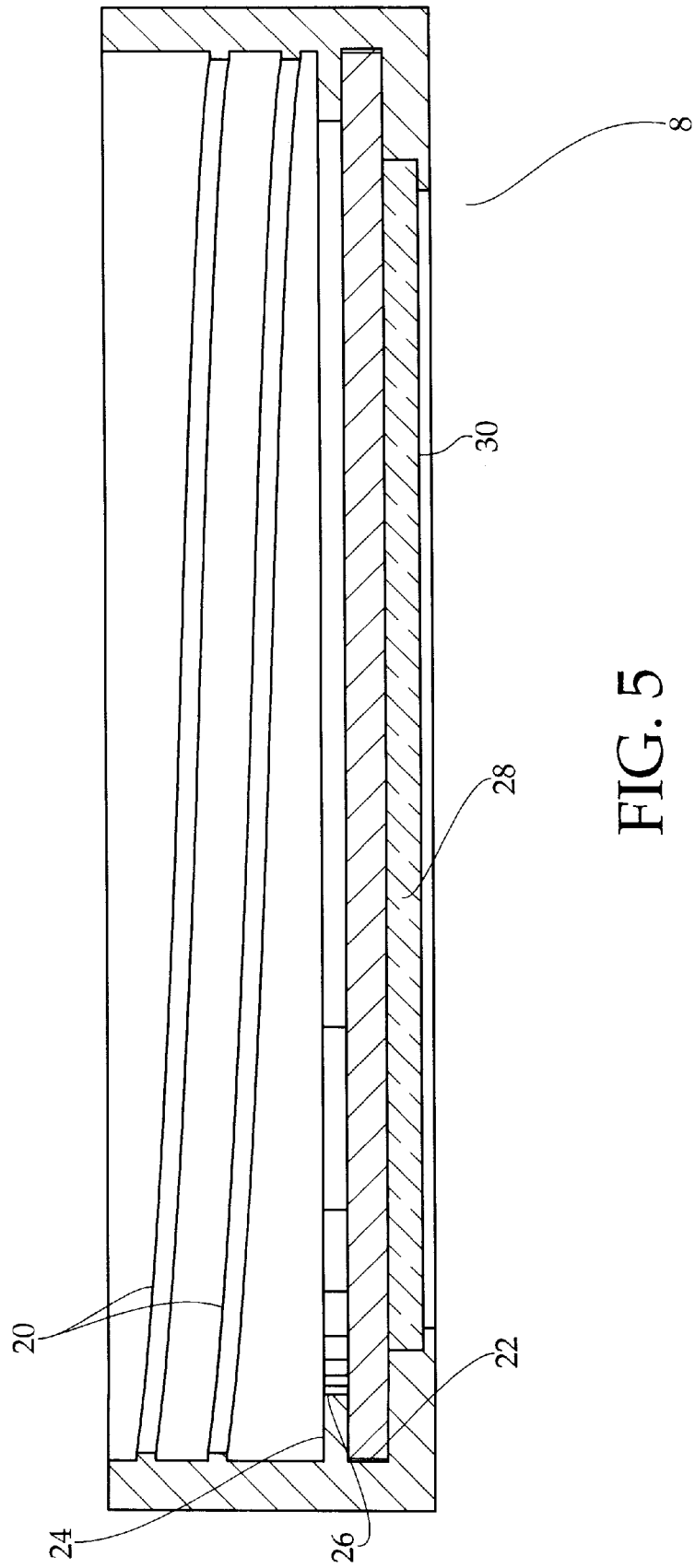
FIG. 5 is a cross sectional view, taken on line 5—5 of FIG. 4, of the collection cup lid.

A second embodiment of the assaying system is seen in FIGS. 3A through 5. The collection cup 10 is illustrated thereat, with the opening 16 located at the upper end 12, and screw threads 20 disposed about said opening for accepting the collect ion cup lid 18. As depicted in FIG. 5, the collection cup lid 18 of this second embodiment further has an underside w all 24 which comes into contact with and effectively provides a sealing means for sealing the opening 16 when the collection cup lid 18 is screwed onto the collection cup 10 (as seen in FIG. 3B).

The test card 22 is positioned between a plenum 26 and a transparent window 28 as seen in FIG. 5. The plenum 26 is in fluid communication with the underside wall 24 of the collection cup lid 18 and the test card 22. Accordingly, upon placing a volume of physiological fluid such as urine in the collection cup 10, securing the collection cup lid 18 to the collection cup 10 and inverting said assembled collection cup 10 and collection cup lid 18, the contained liquid is permitted to pass through the plenum 26 and contact the test card 22. A window opening 30 is located opposite the underside wall 24, exposing the transparent window 28 and hence the test card 22 located therebehind, as seen in FIG. 4. The volume of urine or other physiological fluid is then analyzed by the test card 22 and visual analysis results are provided thereon, immediately visible through the transparent window 28.

The test card 22 employed by both embodiments of the assaying system possesses assaying means 32 as seen in FIGS. 1 and 4. Said assaying means 32 preferably comprise antibodies and/or reagents capable of chemically analyzing a sample volume of urine to detect a positive presence of a particular substance (such as marijuana, opiates, amphetamines, cocaine, PCP, etc.) In the drawing figures depicting the instant invention, a plurality of individual analysis strips 34 are employed as the assaying means 32, each of said analysis strips 34 capable of indicating the positive presence of distinct illicit substances. Traditionally, said assaying means 32 were configured merely to indicate the positive presence of particular substances. If a "positive" indication was given, it was automatically inferred that the donor individual who provided the urine was a drug user/abuser (although secondary testing is always conducted to confirm these results). This system poses great threats to individual privacy and civil liberty concerns, and hence proves unsatisfactory.

The assaying system of the instant invention contemplates the addition of "control positives" to the assaying means 32. For example, a pre-determined number of assaying systems (5% for instance) could be configured so that a "false" (i.e.

control) positive indication would be given by the assaying means 32 in addition to any true positive results which may be present. All tests not resulting in a positive indication could be handled in one manner (such as the donor individual being offered employment) while all positive results would be forwarded to a secondary testing facility for additional analysis to distinguish "control" positives from true positives. All control positives could then also be handled as though they had tested "negative" (i.e. not positively) initially, and handled accordingly (such as being offered employment at that later time).

By implementing control positives, the anonymity of those donor individuals testing true positive (drug users) would be protected on-site since a certain percentage of all donor individuals will automatically test positive, and it will be indeterminable whether such positive is a true positive or control positive. Only after secondary testing at a removed, confidential facility will the control positives be distinguishable from the true positives.

The test card 22 employed by both embodiments of the assaying system also possesses adulteration detection means 36, as seen in FIGS. 1 and 4. Said adulteration detection means 36 are capable of determining whether a particular specimen of urine or other physiological fluid has been tampered with by administering either chemical analysis (to ensure that the chemical composition of said specimen is consistent with that of standard, non-adulterated human urine) and/or temperature analysis (to ensure that the specimen has been recently excreted from the donor and has not been brought to the test site by the donor from an earlier excretion). Furthermore, quality control indication means 38 are also present upon said test cards 22 to ensure that the assaying means 32 are functioning properly. Said quality control indication means 38 are configured to generate a signal upon contact with urine or other physiological fluids to indicate that the assaying means 32 have not been degraded due to improper storage, etc. If the quality control indication means 38 fail to generate a signal upon contact with the urine, the test card 22 and/or collection cup lid 18 should be discarded.

The aforementioned configuration of both embodiments of the assaying system of the instant invention render said system capable of being employed on-site at an employer's individual location. A donor individual is given a collection cup 10, and provided a private environment where said donor individual is to excrete a specimen volume of urine into the collection cup 10 for analysis. The collection cup lid 18 is then secured to the collection cup 10, and the assembly is then shaken vigorously. The quality control indication means 38 are then checked to assure the integrity of the assaying means 32. Assuming that the quality control indication means 38 signal that the assaying means 32 are functioning properly, the adulteration detection means 36 are then checked to determined whether the donor individual tampered with the specimen or provided an external specimen. If the adulteration detection means 36 indicate that the specimen is unadulterated, then the assaying means 32 such as the analysis strips 34 are checked.

The donor individuals who provided negative results may be offered employment if the employer so wishes. All positive indications are sent to a laboratory for further analysis so that the true positives may be distinguished from the control positives. Upon determining this distinction, the names of the donor individuals whose results were control positives can be forwarded to the employer, so that the employer may offer these individuals employment if desired. Accordingly, the employer is immediately provided with a number of qualified potential employees to chose from, and the privacy concerns of the donor individual are safeguarded.

What is claimed is:

1. An assaying system for detecting the absence of illicit substances in human physiological fluids such as urine, said fluids emanating from a donor individual, comprising:

a) assaying means for chemically analyzing the human physiological fluid to detect an absence of illicit substances therein, said assaying means comprising intentionally-added control positives such that a predetermined percentage of said assaying means are configured to falsely signal a positive detection of illicit substances, thus making it impossible to distinguish true test-positive donor individuals from control-positive donor individuals, and thus initially preserving the anonymity of said true test-positive donor individuals until further analysis is conducted; and b) quality control indication means to ensure that the assaying means are functioning properly.

2. The assaying system of claim 1, further comprising adulteration detection means for determining whether the physiological fluid provided by the donor individual has been tampered with.

3. The assaying system of claim 2, wherein the adulteration detection means further comprise the employment of chemical analysis to verify the integrity of the physiological fluid by ensuring that the chemical composition of said fluid is consistent with that of identical non-adulterated physiological fluids, and the employment of temperature analysis to verify that the fluid is of a temperature which indicates that it has been recently excreted from the donor.

4. The assaying system of claim 3, wherein said assaying means, adulteration detection means and quality control indication means are located upon a test card.

5. The assaying system of claim 4, wherein the assaying means comprise a plurality of individual analysis strips, each of said analysis strips capable of indicating the positive presence of distinct illicit substances.

6. The assaying system of claim 5, further comprising a collection cup having an upper end, a lower end, an opening located at the upper end, screw threads formed into the collection cup proximate the opening at the upper end for accepting the collection cup lid, and further having the test card affixed to said collection cup lid such that physiological fluid from the donor individual may be deposited into the collection cup prior to the collection cup lid being affixed thereto, the collection cup then shaken vigorously to wash the test card in the fluid, and indicated results then visually observed therefrom.

7. The assaying system of claim 6, wherein said collection cup lid further comprises an underside wall, a plenum, and a transparent window, the test card located between said plenum and said transparent window, and the plenum in fluid communication with the underside wall of the collection cup lid and the test card such that by placing a volume of physiological fluid in the collection cup lid, securing the collection cup lid to the collection cup and inverting said assembled collection cup and collection cup lid, the contained fluid is permitted to pass through the plenum and bathe the test card so that the analysis results of the fluid by the test card may be immediately visually observed through the transparent window.

8. A method for detecting the presence of illicit substances in physiological fluids emanating from a donor individual, comprising the steps of:

a) receiving a specimen of physiological fluids from the donor individual;

b) bringing a portion of said physiological fluids into contact with quality control indication means, and proceeding to the next step if said quality control indication means indicate a positive result;

c) bringing a portion of said physiological fluids into contact with adulteration detection means, and proceeding to the next step if said adulteration detection means indicate that the integrity of the physiological fluid has not been impaired;

d) bringing a portion of said physiological fluids into contact with assaying means to detect the positive presence of illicit substances in said fluid, said assaying means configured such that a pre-determined percentage of said assaying means will falsely signal a positive indication of illicit substances; and e) further analyzing all positive results detected by the assaying means to distinguish the true positive results from the control positive results.

9. The method of claim 8, wherein:

a) the specimen of physiological fluid received from the donor individual is deposited by said donor individual into a collection cup, and a collection cup lid having a test card possessing assaying means, adulteration detection means and quality control indication means embedded thereupon is affixed to the collection cup lid;

b) the assembled collection cup and collection cup lid are shaken; and c) the analysis results provided upon the test card are read visually therefrom.

* * * * *